US008501810B2

(12) United States Patent
Gastner et al.

(10) Patent No.: US 8,501,810 B2
(45) Date of Patent: Aug. 6, 2013

(54) GUANIDINO ACETIC ACID USED AS AN ANIMAL FOOD ADDITIVE

(75) Inventors: Thomas Gastner, Engelsberg (DE); Hans-Peter Krimmer, Kirchweidach (DE)

(73) Assignee: AlzChem Trostberg GmbH, Trostberg (DE)

( * ) Notice: Subject to any disclaimer, the term of this patent is extended or adjusted under 35 U.S.C. 154(b) by 0 days.

(21) Appl. No.: 13/164,973

(22) Filed: Jun. 21, 2011

(65) Prior Publication Data

US 2011/0257075 A1    Oct. 20, 2011

Related U.S. Application Data

(63) Continuation of application No. 11/596,771, filed as application No. PCT/EP2005/006110 on Jun. 7, 2005, now abandoned.

(30) Foreign Application Priority Data

Jun. 9, 2004  (DE) .......................... 10 2004 028 193
Dec. 11, 2004 (DE) .......................... 10 2004 059 761

(51) Int. Cl.
*A61K 31/195*   (2006.01)
*A61K 31/198*   (2006.01)
*A61K 31/155*   (2006.01)
*A23K 1/16*     (2006.01)
*A23K 1/18*     (2006.01)
*A23L 1/30*     (2006.01)

(52) U.S. Cl.
USPC ......................................... 514/565; 426/648

(58) Field of Classification Search
USPC ......................................... 514/565; 426/648
See application file for complete search history.

(56) References Cited

U.S. PATENT DOCUMENTS

| | | | |
|---|---|---|---|
| 2,620,354 A | 12/1952 | Vassel et al. | |
| 2,654,779 A | 10/1953 | Vassel et al. | |
| 3,089,771 A | 5/1963 | Hopper | |
| 3,843,798 A * | 10/1974 | Cook et al. ............... | 514/565 |
| 5,032,410 A | 7/1991 | Furukawa et al. | |
| 5,863,939 A | 1/1999 | Pischel et al. | |
| 6,172,111 B1 | 1/2001 | Pischel et al. | |
| 6,413,962 B1 * | 7/2002 | Naftchi ..................... | 514/245 |
| RE38,155 E | 6/2003 | Brown et al. | |
| 7,226,947 B1 | 6/2007 | Wallimann et al. | |
| 2004/0043105 A1 | 3/2004 | Miura et al. | |
| 2004/0054006 A1 | 3/2004 | Kaddurah-Daouk et al. | |
| 2005/0287204 A1 | 12/2005 | Hageman et al. | |

FOREIGN PATENT DOCUMENTS

| | | |
|---|---|---|
| DE | 738131 C | 8/1943 |
| DE | 24 41 777 A1 | 3/1976 |
| DE | 206735 A1 | 2/1984 |
| DE | 29 37 358 C2 | 9/1987 |
| DE | 197 07 694 A1 | 8/1998 |
| DE | 198 36 450 A1 | 2/2000 |
| DE | 100 03 835 A1 | 8/2001 |
| EP | 0 8904 083 B1 | 11/1999 |
| GB | 2 300 103 A | 10/1996 |
| WO | WO 91/07954 A1 | 6/1991 |
| WO | WO 00/67590 A1 | 11/2000 |
| WO | WO 01/00212 A1 | 1/2001 |
| WO | WO 2004/000297 A1 | 12/2003 |

OTHER PUBLICATIONS

Michiels, J. et al., "Supplementation of guanidinoacetic acid to broiler diets: effects on performance, carcass characteristics, meat quality, and energy metabolism," Poultry Science, vol. 91, pp. 402-412 (2012).*
HCAPLUS abstract 2010:1567735, abstracting CN 101912044 (2010).*
Francaux, et al. "Effect of Exogenous Creatine Supplementation on Muscle PCr Metabolism", *Int. J. sports Med* (2000) 21, pp. 139-145.
Greenhaff, Paul L. "Factors Modifying Creatine Accumulation in Human Skeletal Muscle", Kluwer Acad. Publ. (2000) pp. 75-82.
McKittrick D.S. "The Interrelations of Choline and Methionine in Growth and the Action of Betaine in Replacing Them", Univ. of Berkeley, CA (1946) pp. 133-155.
Poutsiaka, John W. "Relationship Between Growth and Muscle Creatine Levels in Young Rats Fed Supplementary Folacin, $B_{12}$ and Methylating Agents With and Without Glycocyamine", Fordham Univ., New York City (1955) pp. 565-567.
Almquist,et al. "Creatine formation in the chick", www.jbc.org, (1941) pp. 365-373.
Harada, Katsuhiko "Studies on the feeding attractants for fishes and shellfishes-XV.[..]", CAPLUS Abstract 108:72574m (1987), 53912), 2241-5.
Keshavarz, et al. "Relationship of Arginine and Methionine to Creatine Formation in Chicks", *J. Nutrition*, 101 (1970), pp. 855-862.

* cited by examiner

*Primary Examiner* — John Pak
(74) *Attorney, Agent, or Firm* — Fulbright & Jaworski LLP

(57) ABSTRACT

The present invention relates to the use of guanidinoacetic acid and/or salts thereof as feed additive, in predominantly vegetarian diets, in particular use being made of salts with hydrochloric acid, hydrobromic acid and phosphoric acid. The use proceeds especially in individual doses from 0.01 to 100 g/kg of feed in the form of powders, granules, pastilles or capsules, the feed additive also being able to be used in combination with other physiologically active materials of value. The claimed use which is suitable especially for breeding and growing livestock, has recourse to a compound which is in particular stable in aqueous solution, can be converted to creatine under physiological conditions, and, in contrast to other guanidine derivatives, is completely available to physiological sectors of use.

35 Claims, No Drawings

GUANIDINO ACETIC ACID USED AS AN ANIMAL FOOD ADDITIVE

This application is a continuation of U.S. Ser. No. 11/596,771 filed Nov. 17, 2006 now abandoned, which is a §371 of PCT/EP2005/006110 filed Jun. 7, 2005, hereby incorporated by reference in its entirety. This application also claims priority from DE 10 2004 028 193.9 filed Jun. 9, 2004 and DE 10 2004 059 761.8 filed Dec. 11, 2004.

The present invention relates to the use of guanidinoacetic acid or of salts of guanidinoacetic acid as feed additive.

Guanidinoacetic acid is an endogenous substance in animals and humans which takes a central role in the biosynthesis of creatine. Creatine can be both taken by the diet, and also formed endogenously. Its biosynthesis proceeds from glycine and L-arginine. In mammals, primarily in the kidneys, but also in the liver and pancreas, the guanidino group of the L-arginine is cleaved by the enzyme aminotransferase and an N-C-N group is transferred to the glycine. The L-arginine is converted in this case to L-ornithine. The guanidinoacetic acid thus formed is converted in the next step to creatine using the enzyme transmethylase, in vertebrates this takes place exclusively in the liver. Here, the S-adenosylmethionine acts as methyl group donor. Creatine then diffuses into the blood circulation and is thus transported to the target organs. Transport through the cell membrane into the cells takes place in this case via a specific creatine transporter.

It is also known in guanidinoacetic acid that it possesses antibacterial activity and has been successfully used in animal experiments against bacterial infections (*Staphyllococcus aureus*) (Preparation for protecting mammals against infection (Stanley Drug Products Inc., USA). Neth. Appl. (1976), 7 pp. NL 7411216).

K. Keshavarz and H. L. Fuller describe in Journal of Nutrition, 101: 855-862 (1971) the action of arginine and methionine on creatine formation in chicks. The base feeds used in this connection had been admixed, inter alia, also with 1.112% guanidinoacetic acid (glycocyamine), which subsequently, also in combination with methionine, has led to a significant decrease in the weight gain and feed utilization.

In connection with overdose of methionine, on the other hand, it is known that adverse effects connected therewith can be mitigated by administering guanidinoacetic acid (Interrelations of choline and methionine in growth and the action of betaine in replacing them. McKittrick, D. S. Univ. of California, Berkeley, Archives of Biochemistry (1947), 15 133-55).

The abovementioned creatine takes an important role in the energy metabolism of the cell, it being, as high-energy phosphocreatine, in addition to adenosin triphosphate (ATP), an important energy reserve of muscle. In the resting state of muscle, ATP can transfer a phosphate group to creatine, phosphate creatine being formed which is then in direct equilibrium with ATP. During muscular work it is of critical importance to replenish the ATP stores as rapidly as possible. The phosphocreatine is available therefor in the first seconds of maximum muscle load. This phosphocreatine can transfer a phosphate group to adenosin diphosphate by the enzyme creatine kinase in a very rapid reaction and thus reform ATP. This is also termed the Lohmann reaction.

Creatine has long been known as a suitable food and feed supplement. In the case of strenuous and longer-lasting muscle work, the creatine reserves which natural are present in the body are rapidly exhausted. For this reason, in particular in the case of competitive athletes, targeted creatine administration has had beneficial effects on stamina and performance, with unwanted enrichment processes in the body or disadvantageous degradation products being unknown. The reason for this is that creatine is excreted by the body as creatinine in the case of excess supply.

In addition it is known that creatine supplementation leads to increase in body mass. This is at the beginning ascribed to increased uptake of water into the muscle. In the long term, creatine indirectly leads to an increase in muscle mass (Int J Sports Med 21 (2000), 139-145) via increased protein synthesis or a decreased protein catabolism in the myofibrils. As a result increased fat-free body mass is thus obtained.

In addition to creatine itself, that is creatine monohydrate, in the interim, numerous creatine salts such as creatine ascorbate, citrate, pyruvate and others, have likewise proved suitable food supplements. As examples at this point mention may be made of European patent EP 894 083 and German Laid-Open application DE 197 07 694 A1 as prior art.

Creatine also exhibits the effects demonstrated as beneficial to humans in animals, for which reason its use has likewise been sufficiently previously described in diverse feeds. For instance, the international patent application WO 00/67 590 has previously described the use of creatine or creatine salts as feed additive for breeding and growing livestock, as replacement for meat meal, fish meal and/or antimicrobial performance enhancers, growth hormones as well as anabolic agents. GB 2 300 103 teaches the use of creatine in the form of a dog biscuit, for which creatine monohydrate is offered together with meat in an extruded mix. Since creatine monohydrate, owing to its poor solubility, is only insufficiently bioavailable, its joint use together with other physiologically active compounds, preferably in salt form, is recommended. German Laid-Open application DE 198 36 450 A1 has, as subject matter, the use of stable pyruvic acid salts, and in particular creatine pyruvate, in formulations which are suitable for animal nutrition.

DE 100 03 835 A1 has, as subject matter, formulations for dehydration conditions as generally occur in older persons, in particular those having restricted mobility. In this case creatine acts as a transport medium for water in order in this manner to supply moisture to the tissues most severely affected by dehydration symptoms.

In addition to its undisputed beneficial physiological properties, creatine, however, has the disadvantage that, as creatine monohydrate, it does not have pronounced stability in the corresponding aqueous solutions in that it converts itself over a relatively long period into creatinine. This is a problem especially in acidic solutions and is thus also of importance for oral intake and bioavailability of creatine. The pH of the stomach of 1 to 2 can, depending on the residence time, lead to significant breakdown of the creatine to form creatinine. For instance, in humans it has been found that after oral application of creatine, only about 15 to 30% can be resorbed by the musculature (Greenhaff, P. L.: Factors Modifying Creatine Accumulation in Human Skeletal Muscle. In: Creatine, From Basic Science to Clinical Application. Medical Science Symposia Series Volume 14, 2000, 75-82).

Finally, reference may be made to the contribution by John W. Poutsiaka (Department of Biology Fordham University New York; in: American Journal of Physiology). In this article from 1956, the effects of folacin, vitamin $B_{12}$ and methylating compounds are also described in the presence of guanidinoacetic acid on the growth and muscular creatine level in young rats. With respect to growth, the guanidinoacetic acid in this article is ascribed an inhibitory activity. Guanidinoacetic acid had no effect on the muscle creatine level when it was administered in combination with folacin and vitamin $B_{12}$. In the case of additional administration of methionine, the creatine content in the skeletal musculature and in the heart muscle increased. On the basis of these observations, it was concluded that guanidinoacetic acid is formed in the body from arginine and glycine, which are both as amino acids principally responsible for the methionine-supported growth.

The disadvantages of the prior art with respect to creatine have produced the object of the present invention to find compounds which can be used as feeds or feed additive for breeding and growing livestock and have a beneficial effect on improving feed uptake, increasing the growth performance, raising the muscle flesh gain, meat quality and/or the reproduction performance. The compounds should have as low an instability as possible, in particular in aqueous solution, and preferably not be converted into creatine until after application or physiological uptake. The feeds or feed additives used should not themselves develop any physiologically disadvantageous effects and be readily detectable. From commercial aspects, of primary importance for the substances to be used according to the invention was also the fact that they should be able to be produced in an economically expedient manner.

This object has been achieved by the use of guanidinoacetic acid and/or salts of guanidinoacetic acid as feed additive for breeding and growing livestock in predominantly vegetarian diets to improve feed uptake, to increase growth performance, muscle meat gain, meat quality and/or reproduction performance.

The expression used herein "predominantly vegetarian diet" describes a diet which preferably contains no animal components in agreement with the legal directives in the European Union. The only exception in this case is a possible addition of fish meal. In addition, the "predominantly vegetarian diet" according to this invention is also to be taken to mean a partial replacement of fish meal or meat meal by guanidinoacetic acid.

Surprisingly, in the inventive use, it has been found that the claimed compounds in fact have the properties desired according to the object, since they can be produced in a simple and economic manner, for example by methods such as the reaction of glycine and cyanamide in aqueous solutions (Production of guanidino fatty acids (Vassel, Bruno; Janssens, Walter D.) (1952), U.S. Pat. No. 2,620,354; Method of preparation of guanidino fatty acids (Vassel, Bruno; Garst, Roger) (1953), 5pp U.S. Pat. No. 2,654,779).

In contrast to creatine and creatine monohydrate, guanidinoacetic acid and salts thereof in addition exhibit a significantly higher stability in acidic aqueous solution and they are not converted to creatine until under physiological conditions. Surprisingly, it is particularly advantageously proved that the guanidinoacetic acid and salts thereof used according to the invention, in contrast to creatine, are in fact not converted to creatine until after resorption, principally in the liver. Thus in contrast to creatine, the majority of the compounds administered or fed, guanidinoacetic acid and/or salts of guanidinoacetic acid, are not degraded by instability reactions, for example in the stomach, and excreted before resorption, but are in fact available in the corresponding physiological metabolic reactions.

Guanidinoacetic acid and salts thereof can be used according to the invention, but again in contrast to creatine and derivatives thereof, with identical activity at significantly lower dosage. The advantages of the use claimed by the invention could not be predicted in their totality, in particular because guanidinoacetic acids, for example in chicks, had been ascribed adverse activity on feed utilization and weight gain.

The claimed use of guanidinoacetic acid and salts thereof as feed additive has proved very effective, for example, for poultry such as, for example, chicks, turkeys, ducks and geese, but also for pigs.

The present invention, in another embodiment, provides using guanidinoacetic acid and/or suitable salts thereof as supplementation or alternatively as feed additive in aquacultures, preferably as partial or total replacement of fish meal and/or antimicrobial performance enhancers, whereas the proposed use being preferred for salmon types (Salmonides) and shrimp types (Natania).

Antimicrobial performance enhancers are substances such as, for example, carbadox, olaquindox, salinomycin, monensin, avilamycin or flavomycin. These are used in particular to prevent the spread of diseases in animals. Further, increased efficiency in animal production shall be achieved. Antimicrobial performance enhancers are also used to avoid transmission of the zoonoses to humans and thus enable the production of high quality and safe animal foods.

The present invention also relates to the use of guanidinoacetic acid and/or salts thereof for the production of a therapeutic composition for breeding and growing livestock which can be used to strengthen the immune system and to improve reproduction performance.

The described therapeutic composition, in a preferred embodiment, is preferably used in poultry and/or pigs.

For the purposes of the present invention, in principle all guanidinoacetic acid salts are suitable which are acceptable in terms of nutritional physiology. For the use according to the invention, in particular salts of guanidinoacetic acid have proved expedient which are obtained with hydrochloric acid, hydrobromic acid and phosphoric acid. Mixtures of guanidinoacetic acid with one or more of these salts or else mixtures of the salts with one another can also be used.

As a further advantage of the use according to the invention it has proved that guanidinoacetic acid and salts thereof can be used in a wide dose range. Daily doses in chicks, per kg of live mass, are, for example, in the range between about 10 mg and about 1200 mg, in particular in the range from about 50 mg to about 250 mg. Individual doses are generally in the range from about 10 mg and about 600 mg, preferably in the range from about 25 to about 125 mg. In the case of pigs, daily doses, per kg of live mass, are, for example, in the range from about 10 mg and about 1000 mg, in particular in the range from about 25 mg to about 150 mg. Individual doses are generally in the range from about 10 mg and about 500 mg, preferably in the range from about 10 mg to about 500 mg, preferably in the range from about 10 to 100 mg.

With respect to the described use as feed additive, depending on animal species, preferably doses of about 0.01 to about 100 g/kg of feed or therapeutic composition come into consideration, amounts from about 1.0 to about 5.0 g being considered as particularly preferred.

Since the claimed use is preferably performed in the non-veterinary field of use, application forms of feed additives have proved particularly suitable which represent powders, granules, pastilles, capsules, pellets or gel (hydrocolloid) products. It is preferred here, depending on the respective specific application, to use guanidinoacetic acid and salts thereof as feed additive in combination with other physiologically active compounds, in particular carbohydrates, fats, amino acids (e.g. creatine), proteins, vitamins, minerals, trace elements and derivatives thereof and any desired mixtures thereof being particularly suitable. Preference is given to methionine, betaine and choline and also other physiologically active methyl group donors. Betaine and choline, in the presence of homocysteine, can be converted to methionine in the body, which especially plays a role in the synthesis of creatine from guanidinoacetic acid. Here, methyl groups are required which are transferred from S-adenosylmethionine with formation of homocysteine. If betaine or choline are insufficiently available, methionine is consumed and a methionine deficit can occur in metabolism.

The mortality of breeding and growing livestock as a result of elevated ambient temperatures is a problem in many countries, especially in summer. In the context of this invention, it has surprisingly been found that supplementation with guanidinoacetic acid or salts thereof leads to mitigation of the consequences of heat stress, in particular to avoiding or decreasing mortality of these animals under heat stress, i.e., for example to a reduction of mortality as a consequence of elevated ambient temperatures. It is assumed that this effect is due to the creatine formed from guanidinoacetic acid, which creatine leads to an improved supply of the affected tissue with water. Similar effects have also already been observed with the use of glycine (US 2004 0043105 A1).

A further aspect of the present invention is thus the use of guanidinoacetic acid and/or salts thereof for production of a composition for breeding and growing livestock for prevention and mitigation of the consequences of heat stress, in particular for reducing mortality as a result of elevated ambient temperatures. In this case the invention provides, in particular, that the therapeutic composition serves in predominantly vegetarian diets as partial and/or total replacement of fish meal, meat meal, anabolic agents (e.g. stilbenes, steroids, thyreostatics and β-agonists), antimicrobial performance enhancers and/or growth hormones.

In addition, guanidinoacetic acid and salts thereof can be used as feed additive for wet and dry feeds for dogs and cats, whereas positive effects result on the immune system and the general status of the animals.

Overall, by means of the present invention, guanidinoacetic acid and salts thereof are supplied to new applications as feeds and feed additive, respectively, in the nutrition of breeding and growing livestock or as therapeutic composition for breeding and growing livestock, which, in contrast to the creatine compounds previously used, have significant and surprising advantages. The examples hereinafter further illustrate the present invention.

EXAMPLES

1. Examples According to the Invention 1.1 A formulation consisting of 5000 mg of guanidinoacetic acid and 5000 mg of insulin was introduced into a typical formula for feed pellets for feed supplementation of horses.

1.2 A formulation consisting of 7000 mg of guanidinoacetic acid and 750 mg of carnitine tartrate was introduced into the base mix for salmon feed.

1.3 As base mixture, the following formulation was introduced homogeneously into commercial pig feed: 3000 mg of guanidinoacetic acid phosphate, 3000 mg of creatine, 40 mg of magnesium stearate, 25 mg of carboxymethylcellulose and 135 mg of lactose.

1.4 Feed for Growing Hens

It was found that the addition of 0.092% by weight of guanidinoacetic acid (0.92 g/kg) to the air-dried feed for 42 days' growing duration produced an increase in the final weight by 7% compared with previous feeding methods without guanidinoacetic acid. This increase in weight was achieved solely by meat gain, but not by fat gain or water accumulation (improvement of the lean-body mass index), the meat also exhibiting improved quality. In addition, with this feed additive, the feed consumption decreased by about 6% compared with previous feeding methods.

In addition, it was found in this experiment that even an addition of 0.032% by weight of guanidinoacetic acid (0.32 g/kg) to the air-dried feed increased the final weight by 3% for 42 days' growing duration. The feed consumption decreased by 3% compared with previous feeding methods. In the control group having an addition of 0.04% by weight of creatine monohydrate (0.4 g/kg) to the air-dried feed, for 42 days' growing duration, in contrast, no increase in the final weight and no decreased feed consumption were observed.

2. Comparative Example (According to EP 920 689)

The effect of the addition of creatine in the feed for growing hens was investigated.

In this study it was found that the addition of 0.2% creatine (2 g/kg) to the air-dried feed over 41 days growing duration produced an increase in the final weight by 4% compared with previous feeding methods (without creatine addition). This increase in weight was achieved only by meat gain, but not by fat gain (improvement of the lean-body mass index), the meat also having an improved quality. The feed consumption decreased by about 2-3% compared with previous feeding methods.

The invention claimed is:

1. A method for improving feed uptake, increasing growth performance, increasing muscle meat gain, increasing meat quality or increasing reproduction performance in a livestock animal comprising:
    administering to the livestock animal a sufficient amount of a feed additive to improve the feed uptake, to increase the growth performance, to increase the muscle meat gain, to increase the meat quality or to increase the reproductive performance of the livestock animal as a part of a predominantly vegetarian diet for the livestock animal,
    wherein the feed additive comprises 0.01 to 100 g of guanidinoacetic acid or a salt thereof per kg of feed.

2. The method of claim 1, wherein the livestock animal is poultry or a pig.

3. The method of claim 1, wherein the salt is a hydrochloric acid salt, a hydrobromic acid salt or a phosphoric acid sail.

4. The method of claim 1, wherein the guanidinoacetic acid or salt thereof is provided as an individual dose of from 1.0 to 5.0 g per kg of feed.

5. The method of claim 1, wherein the composition is in the form of a powder, a granule, a pastille, a capsule, a pellet, a conglomerate or a gel product.

6. The method of claim 1, wherein the composition further comprises a carbohydrate, a fat, an amino acid, a protein, a vitamin, a mineral or a trace element, or a physiologically active methyl group donor.

7. The method of claim 1, wherein the feed is air-dried.

8. A method for breeding and growing a livestock animal to strengthen the immune system and to improve the reproductive performance of the livestock animal comprising
    administering to the livestock animal a sufficient amount of a therapeutic composition comprising guanidinoacetic acid or a salt thereof for breeding and growing the livestock animal to strengthen the immune system of the livestock animal and to improve the reproduction performance of the livestock animal,
    wherein the therapeutic composition is provided in a predominantly vegetarian diet, and wherein the guanidinoacetic acid or salt thereof is present in the therapeutic composition in an amount of from 0.01 to 100 g per kg of the therapeutic composition.

9. The method of claim 8, wherein the livestock animal is poultry or a pig.

10. The method of claim 8, wherein the salt is a hydrochloric acid salt.

11. The method of claim 8, wherein the guanidinoacetic acid or salt thereof is provided as an individual dose of from 1.0 to 5.0 g per kg of the therapeutic composition.

12. The method of claim 8, wherein the composition is in the form of a powder, a granule, a pastille, a capsule, a pellet, a conglomerate or a gel product.

13. The method of claim 8, wherein the composition further comprises a carbohydrate, a fat, an amino acid, a protein, a vitamin, a mineral or a trace element, or a physiologically active methyl group donor.

14. A method for breeding and growing a livestock animal to mitigate a consequence of heat stress comprising
  administering to the livestock animal a sufficient amount of a feed comprising guanidinoacetic acid or a salt thereof for breeding and growing the livestock animal to mitigate the consequence of heat stress,
  wherein the guanidinoacetic acid or salt thereof is present in the feed in an amount of from 0.01 to 100 g per kg of feed, wherein the feed is provided as part of a predominantly vegetarian diet.

15. The method of claim 14, wherein mortality of the livestock animal as a consequence of elevated ambient temperatures is reduced.

16. The method of claim 14, wherein the livestock animal is poultry or a pig.

17. The method of claim 14, wherein the salt is a hydrochloric acid salt, a hydrobromic acid salt or phosphoric acid salt.

18. The method of claim 14, wherein the guanidinoacetic acid or salt thereof is provided as an individual dose of from 1.0 to 5.0 g per kg of feed.

19. The method of claim 14, wherein the composition is in the form of a powder, a granule, a pastille, a capsule, a pellet, a conglomerate or a gel product.

20. The method of claim 14, wherein the composition further comprises a carbohydrate, a fat, an amino acid, a protein, a vitamin, a mineral or a trace element, or a physiologically active methyl group donor.

21. A method for improving feed uptake, increasing growth performance, increasing muscle meat gain, increasing meat quality or increasing reproduction performance in a livestock animal comprising
  administering to the livestock animal a sufficient amount of feed additive to improve feed uptake, increase growth performance, increase muscle meat gain, increase meat quality or increase reproduction performance in the livestock animal as a part of a predominantly vegetarian diet for the livestock animal,
  wherein the feed additive comprises guanidinoacetic acid or a salt thereof and wherein the guanidinoacetic acid or salt thereof is present in the feed in an amount of from 0.01 to 5 g/kg of feed.

22. The method of claim 21, wherein the guanidinoacetic acid or salt thereof is used in doses of from 0.01 to 1.0 g/kg of feed.

23. The method of claim 21, wherein the livestock animal is poultry or a pig.

24. A method for improving feed uptake in a livestock animal comprising
  administering to the livestock animal a sufficient amount of feed additive to improve the feed uptake of the livestock animal as a part of a predominantly vegetarian diet for the livestock animal,
  wherein the feed additive comprises from 0.01 to 100 g of guanidinoacetic acid or a salt thereof per kg of feed, and
  wherein at the same time a feed consumption of the livestock animal decreases.

25. The method of claim 24, wherein the livestock, animal is poultry or a pig.

26. A method for improving feed uptake in a livestock animal comprising
  administering to the livestock animal a sufficient amount of feed additive to improve the feed uptake of the livestock animal as a part of a predominantly vegetarian diet for the livestock animal,
  wherein the feed additive comprises from 0.01 to 100 g of guanidinoacetic acid or a salt thereof per kg of feed.

27. The method of claim 26, wherein the livestock animal is poultry or a pig.

28. A method for increasing growth performance in a livestock animal comprising
  administering to the livestock animal a sufficient amount of feed additive to increase the growth performance of the livestock animal as a part of a predominantly vegetarian diet for the livestock animal,
  wherein the feed additive comprises from 0.01 to 100 g of guanidinoacetic acid or a salt thereof per kg of feed.

29. The method of claim 28, wherein the livestock animal is poultry or a pig.

30. A method for increasing muscle meat gain in a livestock animal comprising
  administering to the livestock animal a sufficient amount of feed additive to increase the muscle meat gain in the livestock animal as a part of a predominantly vegetarian diet for the livestock animal,
  wherein the feed additive comprises from 0.01 to 100 g of guanidinoacetic acid or a salt thereof per kg of feed.

31. The method of claim 30, wherein the livestock animal is poultry or a pig.

32. A method for increasing meat quality in a livestock animal comprising
  administering to the livestock animal a sufficient amount of feed additive to increase the meat quality in the livestock animal as a part of a predominantly vegetarian diet for the livestock animal,
  wherein the feed additive comprises from 0.01 to 100 g of guanidinoacetic acid or a salt thereof per kg of feed.

33. The method of claim 32, wherein the livestock animal is poultry or a pig.

34. A method for increasing reproduction performance in a livestock animal comprising
  administering to the livestock animal a sufficient amount of feed additive to increase the reproduction performance in the livestock animal as a part of a predominantly vegetarian diet for the animal,
  wherein the feed additive comprises from 0.01 to 100 g of guanidinoacetic acid or a salt thereof per kg of feed.

35. The method of claim 34, wherein the livestock animal is poultry or a pig.

* * * * *